United States Patent [19]

Forssmann et al.

[11] Patent Number: 4,539,989

[45] Date of Patent: Sep. 10, 1985

[54] INJURY-FREE COUPLING AND DECOUPLING OF THERAPEUTIC SHOCK WAVES

[75] Inventors: Bernd Forssmann, Friedrichshafen; Wolfgang Hepp, Immenstaad; Güenter Hoff, Daisendorf; Christian Chaussy, Germering, all of Fed. Rep. of Germany

[73] Assignee: Dornier System GmbH, Friedrichshafen, Fed. Rep. of Germany

[21] Appl. No.: 443,568

[22] Filed: Nov. 22, 1982

[30] Foreign Application Priority Data

Nov. 25, 1981 [DE] Fed. Rep. of Germany ....... 3146626

[51] Int. Cl.³ ............................................ A61B 17/22
[52] U.S. Cl. .................................................. 128/328
[58] Field of Search ................. 128/328, 24 A, 303 R, 128/804

[56] References Cited

U.S. PATENT DOCUMENTS 3,356,086 12/1967 Behney .............................. 128/24 A
4,311,147 1/1982 Hausler .............................. 128/328

FOREIGN PATENT DOCUMENTS 2722252 11/1978 Fed. Rep. of Germany ... 128/24 A
2913251 10/1980 Fed. Rep. of Germany ...... 128/328
862646 3/1961 United Kingdom ................ 128/804

Primary Examiner—Lee S. Cohen
Attorney, Agent, or Firm—Ralf H. Siegemund

[57] ABSTRACT

An improved instrument for destroying concretions within the body of living tissue, with a focusing chamber which is a part of an ellipsoid of revolution and at one focus of which shock waves are generated by arc discharge, the improvement comprising that a pad (8) filled with degassed water and of which the front and rear sides thereof (10 and 12 respectively) are composed of shape-adapting, acoustically matched thin foils, is located between the liquid-filled focusing chamber (16) and the coupling site (6) to the body (2), the pad permitting simultaneous introduction of X-rays or ultrasonic waves to locate the concretion and to monitor the success in comminuting, and a second water pad (24) similar to the first pad is located at the body decoupling site and encloses the body over a large area, the rear side thereof being fastened by means of a damping or diffusely reflecting layer (26), for instance foam rubber, to a rigid dish (28) composed of one or more parts.

6 Claims, 1 Drawing Figure

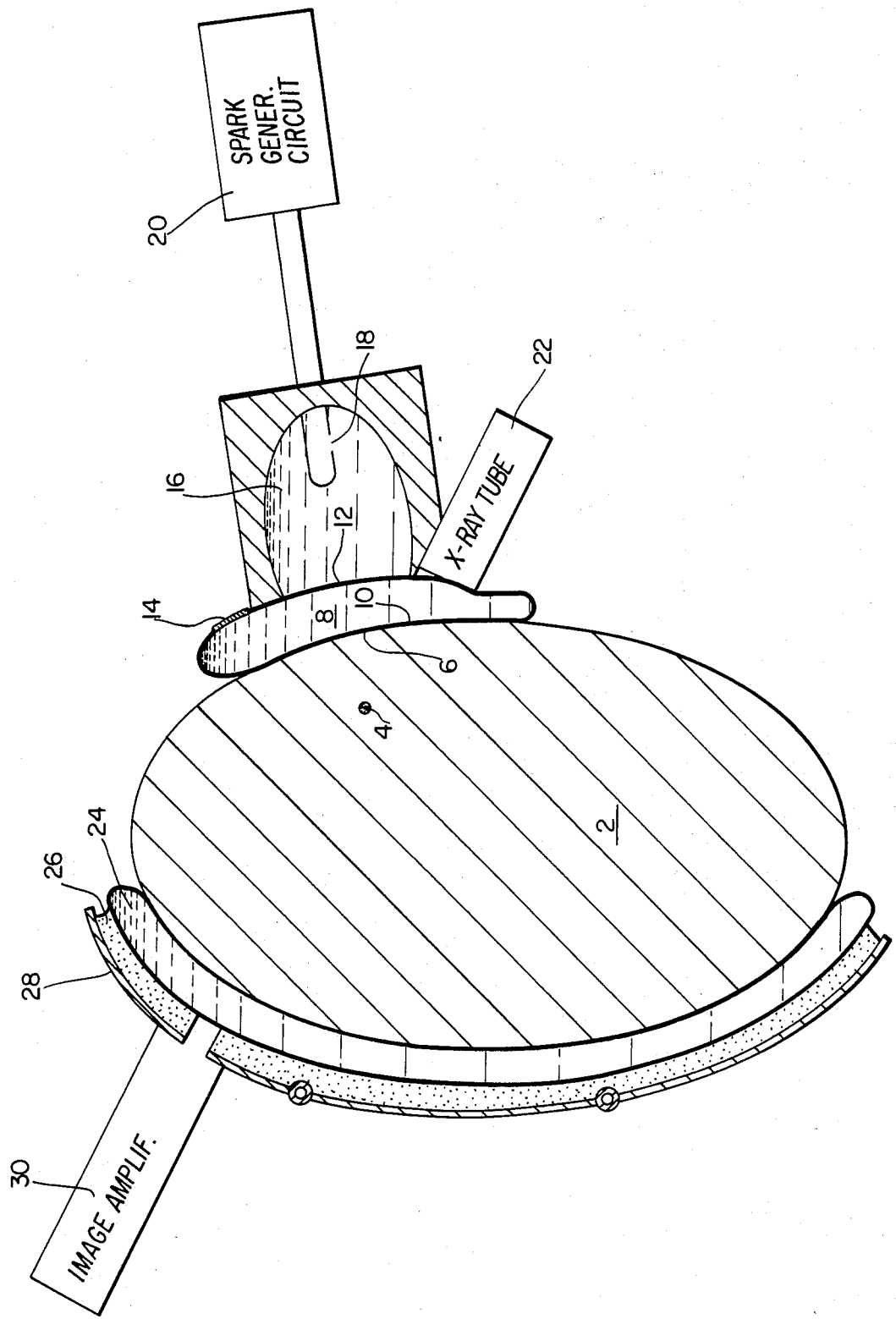

INJURY-FREE COUPLING AND DECOUPLING OF THERAPEUTIC SHOCK WAVES

BACKGROUND OF THE INVENTION

The invention relates to an instrument for destroying concretions in bodies of living tissue using shock waves generated by arc discharge.

One application is the contact-free comminution of kidney stones.

An instrument for the contact-free comminution of concretions in the body of living tissues by means of shock waves is known from U.S. Pat. No. 3,942,531. It is the property of shock waves to exert pressure and tension on the boundary surfaces between media of different acoustic impedances and to be partially reflected. When passing from a biological tissue to a kidney stone, pressure and tension stresses therefore are exerted respectively at the front and rear sides of the stone which is comminuted thereby. When shock waves are introduced from the outside into the body, the patient's skin also forms such a boundary surface with respect to the surrounding air, and high stresses and reflections do take place at this surface. To prevent injury to the skin, the coupling and decoupling sites of the shock waves must abut a medium with an acoustic wave impedance similar to that of the body.

A known solution is to position the body in a tub with degassed water (*Beitraege Zur Urologie*, Volume 2, page 64). This makes the instrument very bulky, the positioning of the patient is cumbersome, and the locating of the concretion, for instance by X-rays, furthermore, is rendered more difficult.

German Offenlegungsschrift No. 2,913,251, discloses a means for destroying kidney stones which is directly placed on the kidney after surgical intervention on the patient. Accordingly, the distance between the instrument and the kidney stone is very small, and the significant coupling site is only a few square centimeters. The shock waves are directly coupled into the organ by means of a small pouch of water acting as the coupling path and being of a few millimeters thickness. However, the narrowness of this design makes impossible the simultaneous checking of the centering, proper abutting and occurrence of destruction. The problem of injury-free decoupling of the shock waves from the body—as these shock waves do not pass all of their energy into the stone—is not disclosed in this German Offenlegungsschrift.

DESCRIPTION OF THE INVENTION

It is the object of the present invention to provide an instrument for the contact-free and non-penetrating comminution of concretions within bodies of living tissue, where focused shock waves generated by arc discharge are coupled into the body and are also decoupled therefrom over a large area and with low losses, in the absence of injury to the body, and where simultaneous monitoring of proper abutting, centering, and success of comminution is possible.

This problem is solved in that a pad filled with degassed water and composed at its front and rear sides of a shape-adapting, acoustically matched, thin foil, is located between the liquid-filled focusing chamber and the coupling site to the body, this pad at the same time permitting the introduction of X-rays or ultrasonic waves for locating the concretions and to monitor the success of the comminution. A second water pad similar to the first one is located at the body decoupling site and encloses the body in a large-area manner, the rear side of which pad is fastened by means of a damping or diffusely reflecting layer (for instance foam rubber) to a rigid dish composed of one or more parts. Instead of water, the pads may be filled with highly viscous liquids or rubbery substances such as polyurethane, for example.

The instrument of the invention affords the following advantages:
 no surgical intervention
  elimination of the large tub and positioning equipment for the patient rendering access to him more difficult
 simple positioning onto the concretion, the flexible water pad permitting displacing the focusing chamber in all directions,
 simple location of the concretion and monitoring of success by X-rays or ultrasonics.

DESCRIPTION OF THE DRAWINGS

The invention will be further illustrated by reference to the accompanying drawing which shows one embodiment of the instrument of the invention.

The FIGURE shows a cross-section of a portion of a human body 2 containing a concretion 4, for instance a kidney stone. A liquid-filled pad 8 of which the front and rear sides 10 and 12 respectively are composed of thin, flexible, acoustically matched membranes, lies against that part of the skin 6 nearest the concretion 4. The pad is provided on the side with a viewing window 14 to inspect the membrane 10 resting without an air gap against the body site 6. An ellipsoidal, water-filled, focusing chamber 16 with a spark gap 18 at one of its foci joins the membrane 12. The electric circuit for the power supply to the spark gap is consolidated in the housing 20 and is no part of this invention. The flexible pad makes possible to so position the focusing chamber that the second focus of the focusing chamber coincides with the concretion 4. At least one monitoring sensor for the coupled field of shock waves is contained in at least one of the pads. At least two X-ray tubes located within the pad 8 serve for the positioning. The tube 22 is shown in the plane of the drawing. A second liquid-filled pad 24 is located on the opposite side of the body and surrounds a larger body surface. Devices for maintaining a temperature proper for the body is provided in at least one of the pads. This pad is fastened by a damping layer 26, for instance of foam rubber, to a rigid dish 28. In this instance, the dish 28 is composed of several mutually displaceable parts. An image amplifier is coaxial with each of the X-ray tubes and the second pad, the image amplifier 30 being shown in the plane of the drawing. The pads 8 and 24 may be placed against the body 2 with the exclusion of air gaps by means of an acoustically transmitting paste.

To destroy a concretion 4, it is first located by means of the two X-ray tubes 22 and the image amplifiers 30. Then the instrument is positioned in such a manner that the concretion lies in the second focus of the focusing chamber 16. By igniting the spark gap 18, the shock waves are next initiated. These shock waves are guided by the focusing chamber 16 to the concretion 4. Injury-free and low-loss coupling to the body 2 is assured by the acoustically matched pad 8. The shock waves do not transmit their entire energy to the concretion 4, rather they travel, though attenuated, through the body. The pad 24 acoustically matched with the body 2 decouples the shock waves from the body in an injury-free manner. Their energy is dissipated mainly in the damping material 26 and at its two boundary surfaces 24-26 and 26-28.

It will be obvious to those skilled in the art that many modifications may be made within the scope of the present invention without departing from the spirit thereof, and the invention includes all such modifications.

What we claim is:

1. In an instrument system for destroying concretions in a body of living tissue, having a liquid filled focusing chamber including a focusing surface which is a part of an ellipsoid of rotation, there being a shock wave generator in the focusing chamber at one focus thereof for generating shock waves by means of arc discharges, a first pad filled with degassed water and provided for being located between the liquid-filled focusing chamber and a coupling site of the body, the improvement of the system comprising, the front and rear sides of said first pad being composed of shape-adapting, acoustically matched thin foils, the first pad, because of its flexibility, its thinness and the use of transmitting materials, permitting simultaneous introduction of X-rays of ultrasonic waves for locating the concretions and to monitor the success in comminution;

a second liquid filled pad similar to the first pad and provided for being located at a body site for acoustically decoupling from the body shock waves having been transmitted through the body, said second pad having a surface area for enclosing a large area of the body and having a rear side;

a rigid dish; and a damping or diffusely reflecting layer fastening the rear side of said second pad to said dish.

2. An instrument system according to claim 1, in which the rigid dish comprises an integrated input screen of a locating system.

3. An instrument system according to claim 1 the first pad having a window for monitoring, centering and air gap-free abutting of its front side to the body.

4. An instrument system according to claim 1 there being an acoustically transmitting paste on the first and second pads so as to exclude air gaps where the pads are placed against the body.

5. In an instrument system for destroying concretions in a body of living tissue, having a liquid filled focusing chamber including a focusing surface which is a part of an ellipsoid of rotation, there being a shock wave generator in the focusing chamber at one focus thereof for generating shock waves by means of arc discharges, the improvement of the system comprising a first pad filled with a highly viscous liquid and provided for being located between the liquid-filled focusing chamber and a coupling site of the body, the front and rear sides of said first pad being composed of shape-adapting, acoustically matched thin foils, the first pad, because of its flexibility, its thinness and the use of transmitting materials, permitting simultaneous introduction of X-rays or ultrasonic waves for locating the concretions and to monitor the success in comminution;

a second pad also filled with a highly viscous liquid, and provided for being located at a body site for acoustically decoupling from the body shock waves having been transmitted through the body, said second pad having a surface area for enclosing a large area of the body and having a rear site;

a rigid dish; and a damping or diffusely reflecting layer fastening the rear side of said second pad to said dish.

6. In an instrument system for destroying concretions in a body of living tissue, having a liquid filled focusing chamber including a focusing surface which is a part of an ellipsoid of rotation, there being a shock wave generator in the focusing chamber at one focus thereof for generating shock waves by means of arc discharges, the improvement of the system comprising a first pad filled with a rubbery substance and provided for being located between the liquid-filled focusing chamber and a coupling site of the body, the front and rear sides of said first pad being composed of shape-adapting, acoustically matched thin foils, the first pad, because of its flexibility, its thinness and the use of transmitting materials, permitting simultaneous introduction of X-rays or ultrasonic waves for locating the concretions and to monitor the success in comminution;

a second pad also filled with a rubbery substance, and provided for being located at a body site for acoustically decoupling from the body shock waves having been transmitted through the body, said second pad having a surface area for enclosing a large area of the body and having a rear site;

a rigid dish; and a damping or diffusely reflecting layer fastening the rear side of said second pad to said dish.

* * * * *